(12) United States Patent
Thorne et al.

(10) Patent No.: US 7,347,842 B2
(45) Date of Patent: Mar. 25, 2008

(54) SAFETY SHIELD FOR MEDICAL NEEDLES

(75) Inventors: David L. Thorne, Kaysville, UT (US); F. Mark Ferguson, Salt Lake City, UT (US); Donald D. Solomon, North Salt Lake, UT (US)

(73) Assignee: Specialized Health Products Inc., Bountiful, UT (US)

(*) Notice: Subject to any disclaimer, the term of this patent is extended or adjusted under 35 U.S.C. 154(b) by 219 days.

(21) Appl. No.: 11/285,512

(22) Filed: Nov. 22, 2005

(65) Prior Publication Data

US 2006/0074387 A1  Apr. 6, 2006

Related U.S. Application Data

(62) Division of application No. 10/712,570, filed on Nov. 13, 2003, now Pat. No. 6,997,902.

(51) Int. Cl.
*A61M 37/00* (2006.01)
(52) U.S. Cl. .................................... 604/263
(58) Field of Classification Search ............. 604/263, 604/110, 162, 111, 117, 177, 264, 272, 164.08, 604/192–198, 228.01–228.04
See application file for complete search history.

(56) References Cited

U.S. PATENT DOCUMENTS

| | | | |
|---|---|---|---|
| 5,183,468 A | 2/1993 | McLees | 604/164 |
| 5,348,544 A | 9/1994 | Sweeney et al. | 604/192 |
| 5,718,688 A | 2/1998 | Wozencroft | 604/164 |
| 5,879,337 A | 3/1999 | Kuracina et al. | 604/192 |
| 5,951,522 A | 9/1999 | Rosato et al. | 604/177 |
| RE37,110 E | 3/2001 | Hollister | 206/365 |
| RE37,252 E | 7/2001 | Hollister | 206/364 |
| 6,280,420 B1 | 8/2001 | Ferguson et al. | |
| 6,623,458 B2 | 9/2003 | Woehr et al. | 604/192 |
| 6,676,633 B2 | 1/2004 | Smith et al. | 604/110 |
| 6,997,902 B2 * | 2/2006 | Thorne et al. | 604/110 |
| 2002/0072716 A1 | 6/2002 | Barrus et al. | |

* cited by examiner

*Primary Examiner*—Matthew F. Desanto
(74) *Attorney, Agent, or Firm*—Paul S. Evans; Kevin Laurence

(57) ABSTRACT

A needle safety apparatus is disclosed which includes an inner bearing disposed within an outer bearing. The inner bearing is moveable to extend telescopically in a first interior space defined by the outer bearing. A second interior space is defined by the inner bearing, while extendable linkage segments connect the hub to the inner bearing. A hub retains the proximal end of a needle, while the distal end of the needle extends through the second interior space. A wedging portion is movable with the inner bearing and pivots to secure the distal end of the needle within the second interior space when the distal end of the needle is retracted therethrough. A latch may be formed in the outer bearing to obstruct the first interior space and prevent the inner bearing from retracting therethrough.

15 Claims, 15 Drawing Sheets

SAFETY SHIELD FOR MEDICAL NEEDLES

CROSS-REFERENCE TO RELATED APPLICATIONS

This patent application is a divisional application of U.S. patent application Ser. No. 10/712,570, filed in the U.S. Patent and Trademark Office on Nov. 13, 2003 now U.S. Pat. No. 6,997,902 by Thorne et al., the entire contents of this disclosure being hereby incorporated by reference herein.

BACKGROUND

1. Technical Field

The present disclosure generally relates to safety shields for medical needles, and more particularly, to safety shields that are extensible to prevent hazardous exposure to a medical needle.

2. Description of the Related Art

Cross-contamination and infection from potentially fatal diseases transmitted by inadvertent needle sticks have resulted in the development of a wide variety of safety medical needle devices used in the areas of I.V. therapy, phlebotomy, syringes and specialty medical needle devices. These diseases include the HIV virus, several strains of hepatitis and other blood and body fluid borne diseases.

Vascular access ports can be surgically implanted to facilitate removal of bodily fluids, such as, for example, blood for testing. Access ports also provide a temporary site for repeated fluid removal, infusion of intravenous fluids or medication infusion. An access port is typically positioned in a body surface of a patient, such as, for example, the chest or arm, to facilitate disposition of a catheter into a blood vessel.

Typically, port access medical needles, such as a Huber needle, are used with the access ports which are implanted for direct vascular communication. Many Huber needles include an angled cannula shaft having a sharpened tip portion oriented at approximately 90 degrees relative to an attachment portion that connects to a fluid source and/or a fluid receptacle. The angular bend in the cannula shaft allows the attachment portion to be secured to the patient while the access port is employed.

Access ports typically include a septum positioned under the surface of the patient's skin, which is adapted to receive a Huber needle puncture at a percutaneous insertion site. The septum is conventionally fabricated from a thick elastomeric membrane which facilitates needle penetration and covers an inner chamber for the infusion of medication or removal of bodily fluids.

Huber needles may be particularly difficult to remove from a needle access port which can result in hazardous exposure of the needle to a patient and a clinician. This is due, at least in part, to the fact that access port septums exhibit forces associated with needle entry and removal, which are much greater than forces normally associated with other medical needle insertion and removal (e.g., with syringes or phlebotomy needles). "Rebound" injuries are typically encountered with Huber needles because of the force required to overcome resistance of the septum of the access port.

Attempts at overcoming the above retention and resistive forces may result in a reflexive motion (e.g., a jerk) by the clinician removing the needle at the time of extraction, which can contribute to the "rebound" injuries. The reflexive motion may be poorly controlled, oscillatory and, therefore, result in an inadvertent needle stick to the patient and clinician, for example, to a hand which is stabilizing an implanted port. Further, difficulty in removal can force a clinician to make a perpendicular pull, which is transverse to a plane orthogonal to the direction of needle insertion. This can result in injury to the patient and the clinician.

A number of Huber needle safety devices are known. For example, one particular device involves a shield separate from the needle for shielding the needle. These types of devices disadvantageously require manipulation and operation of separate devices for shielding the needle. These devices are also bulky and cumbersome which can affect accuracy of placement during use.

Another known attempt at reducing hazards associated with angled needles is a safety device that includes a collapsible pair of wings engaged by the fingers of a clinician to shield the needle. A drawback of devices of this type is that a narrow surface area presses against a patient's skin during withdrawal, which can cause significant pain and discomfort.

The prior art devices may not adequately and reliably shield port access needles to prevent hazardous exposure. A continuing need exists to overcome the disadvantages and drawbacks of the prior art and provide a more adequate and reliable safety apparatus for angled needle devices which sheaths a needle upon removal from an insertion site. Such a safety apparatus may be actuated without applying substantial transverse forces to the needle during removal.

Therefore, it would be desirable to have a safety apparatus for port access needle devices that sheaths a needle upon removal from an insertion site. It would be highly desirable if the safety apparatus was actuated without applying substantial transverse forces to the needle during removal.

SUMMARY

A needle safety apparatus is disclosed which includes an inner bearing disposed within an outer bearing. The inner bearing is moveable to extend telescopically in a first interior space defined by the outer bearing. A second interior space is defined by the inner bearing. A hub retains the proximal end of a needle. The distal end of the needle extends through the second interior space. Extendable linkage segments connect the hub to the inner bearing. A wedging portion is movable with the inner bearing and pivots through the second interior space when the distal end of the needle is retracted therethrough. The wedging portion thereby prevents further proximal motion of the inner bearing. A latch may be formed in the outer bearing to obstruct the first interior space and prevent the inner bearing from retracting distally therethrough.

Objects and advantages of the present disclosure are set forth in part herein and in part will be obvious therefrom, or may be learned by practice of the present disclosure, which is realized and attained by means of the instrumentalities and combinations pointed out in the appended claims. The apparatus and methods of the present disclosure consist of novel parts, constructions, arrangements, combinations, steps and improvements herein shown and described.

The safety apparatus can provide shielding of a sharpened tip of a port access medical needle, such as, for example, a Huber type safety needle, having a sharpened tip at one end and be firmly affixed within a needle hub at the other end during withdrawal from an insertion site. Extraction of the needle from the insertion site may require forces significantly greater than forces associated with extracting other medical needles, such as hypodermic syringes or phlebotomy. Thus, the safety apparatus can include a shield assembly having a finger pad for application of restraining forces about the insertion site. The finger pad spreads digitally applied forces to stabilize the implanted portion of the needle.

The shield assembly contains an inner bearing through which the needle travels during needle extraction. An inner bearing is hingedly affixed to the hub via an extendable frame for articulation along the needle during needle extraction. The sharpened tip of the needle is retracted into the inner bearing forming a latched structure of the inner bearing, outer bearing, extendable segments, needle, and hub. The wedging portion secures or occludes the needle tip within the inner bearing. A latch may engage the inner bearing to maintain the rigid structure in a protective configuration about the sharpened tip. Thus, the needle is extracted and shielded without applying substantial transverse forces to the needle.

In an illustrative embodiment, a needle safety apparatus includes an outer bearing having a sidewall defining a first interior space about a longitudinal axis. An inner bearing has a sidewall defining a second interior space about the longitudinal axis. The inner bearing is disposed in the first interior space and moveable therein along the longitudinal axis. A wedging portion is movable with the inner bearing to secure the needle tip within the second interior space.

In one embodiment, the needle safety apparatus includes a needle disposed in the second interior space and movable along the longitudinal axis. The needle has a distal end including a needle tip. In one embodiment, the needle distal end is mounted to a hub and the hub is connected to the inner bearing by extendable linkage segments.

In at least one embodiment, the needle safety apparatus according the wedging portion is pivotably mounted to said inner bearing. The wedging portion can include a cam surface, which engages the outer bearing sidewall to pivot the wedging portion when the inner portion is moved along the longitudinal axis.

In one embodiment of the needle safety apparatus, the wedging portion is pivotably mounted to the interior bearing, which includes a cam surface that engages the outer bearing sidewall. Engagement between the cam surface and the outer bearing sidewall pivots the wedging portion when the inner bearing is moved along the longitudinal axis to secure the needle tip within the second interior space.

In an illustrative embodiment of the needle safety apparatus, the inner bearing moves telescopically in the first interior space in response to proximal movement of the hub and extension of the extendable linkage segments.

In still another embodiment of the needle safety apparatus, the outer bearing sidewall includes a cutout extending at least partially therethrough. The cutout provides clearance for the wedging portion when the wedging portion is pivoted away from the second interior space. The cutout has a distal surface which engages the cam surface to pivot the wedging portion.

In one embodiment, the outer bearing includes a latching arm extending into the first interior space to latch the inner bearing in a proximal position when the inner bearing is moved proximally along the longitudinal axis beyond the latching arm. The wedging portion is thereby retained in a pivoted position closing the second interior space.

In a particular embodiment, a needle safety apparatus includes an outer bearing having a sidewall defining a first interior space about a longitudinal axis. An inner bearing has a sidewall defining a second interior space about the longitudinal axis. The inner bearing is disposed in the first interior space and moveable therein along the longitudinal axis. A needle is disposed in the second interior space and is movable along the longitudinal axis. A wedging portion is pivotably mounted to the interior bearing and movable with the inner bearing to secure the needle tip within the second interior space. The needle has a distal end including a needle tip and a proximal end mounted to a hub. The hub is connected to the inner bearing by extendable linkage segments.

The inner bearing moves telescopically in the first interior space in response to proximal movement of the hub and extension of the extendable linkage segments. The wedging portion includes a cam surface which engages the outer bearing sidewall to pivot the wedging portion when the inner portion is moved along the longitudinal axis to secure the needle tip within the second interior space. The outer bearing sidewall includes a cutout extending at least partially therethrough. The cutout provides clearance for the wedging portion when the wedging portion is pivoted away from the second interior space. The cutout includes a distal surface which engages the cam surface to pivot the wedging portion. The outer bearing includes a latching arm extending into the first interior space to latch the inner bearing in a proximal position when the inner bearing is moved proximally along the longitudinal axis beyond the latching arm. The wedging portion is thereby retained in a pivoted position securing the needle tip within the second interior space.

In another embodiment of the needle safety apparatus, the outer bearing includes a distal end having a planar surface substantially orthogonal to the longitudinal axis. The needle includes a proximal end and a bend of about 90 degrees between said proximal and distal ends. The hub includes a winged portion extending therefrom, which provides a surface area for gripping.

In a particular embodiment, the needle safety apparatus is a Huber type safety needle. The particular embodiment includes an outer bearing having a sidewall defining a first interior space about a longitudinal axis. An inner bearing has a sidewall defining a second interior space about the longitudinal axis. The inner bearing is disposed in the first interior space and moveable therein along the longitudinal axis. A needle is disposed in the second interior space and movable along the longitudinal axis. A wedging portion is pivotably mounted to the interior bearing and movable with the inner bearing to secure the needle tip within the second interior space. The needle has a distal end including a needle tip and a distal end mounted to a hub. The hub is connected to the inner bearing by extendable linkage segments.

The inner bearing moves telescopically in the first interior space in response to proximal movement of the hub and extension of the extendable linkage segments. The wedging portion includes a cam surface, which engages the outer bearing sidewall to pivot the wedging portion when the inner portion is moved along the longitudinal axis to secure the needle tip within the second interior space. The outer bearing sidewall includes a cutout extending at least partially therethrough, which provides clearance for the wedging portion when the wedging portion is pivoted away from said second interior space. The cutout includes a distal surface which engages the cam surface to pivot the wedging portion. The outer bearing includes a latching arm extending into the first interior space to latch the inner bearing in a proximal position when the inner bearing is moved proximally along the longitudinal axis beyond the latching arm. The wedging portion is thereby retained in a pivoted position closing the second interior space. The outer bearing includes a distal end having a planar surface substantially orthogonal to the longitudinal axis. The needle includes a proximal end and a bend of about 90 degrees between the proximal and distal ends and a tube attached to the proximal end. The hub includes a winged portion extending therefrom providing a surface area for gripping.

In an illustrative embodiment, the needle safety apparatus includes a hub connected to the inner bearing by extendable linkage segments. The inner bearing moves telescopically in the first interior space in response to proximal movement of the hub and extension of the extendable linkage segments. The hub includes a sidewall defining a cavity and proximal end forming a luer fitting.

In another embodiment of the needle safety apparatus, the outer bearing includes a latching arm extending into the first interior space to latch the inner bearing in a proximal position when the inner bearing is moved proximally along the longitudinal axis beyond the latching arm. The wedging portion is thereby retained in a pivoted position securing the needle tip within the second interior space.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings, wherein:

DETAILED DESCRIPTION OF THE EXEMPLARY EMBODIMENTS

The exemplary embodiments of the needle safety apparatus and methods of operation disclosed are discussed in terms of medical needles for infusion of intravenous fluids, medication infusion or fluid collection, and more particularly in terms of needle apparatus that prevent hazardous exposure to the needle including, for example, inadvertent needle stick. It is contemplated that the needle may be shielded during use including storage, transport, fluid infusion and/or collection, subsequent thereto, etc. It is envisioned that the present disclosure, however, finds application to a wide variety of needles and devices for the infusion of preventive medications, medicaments, therapeutics, etc. to a subject. It is also envisioned that the present disclosure may be employed for collection of body fluids, including, those employed during procedures relating to phlebotomy, digestive, intestinal, urinary, veterinary, etc.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the safety shield apparatus. According to the present disclosure, the term "clinician" refers to an individual administering an infusion, performing fluid collection, installing or removing a needle cannula from a safety shield apparatus and may include support personnel.

The following discussion includes a description of the needle safety apparatus, followed by a description of the method of operating the needle safety apparatus in accordance with the present disclosure. Reference will now be made in detail to the exemplary embodiments of the disclosure, which are illustrated in the accompanying figures.

Figure 1:
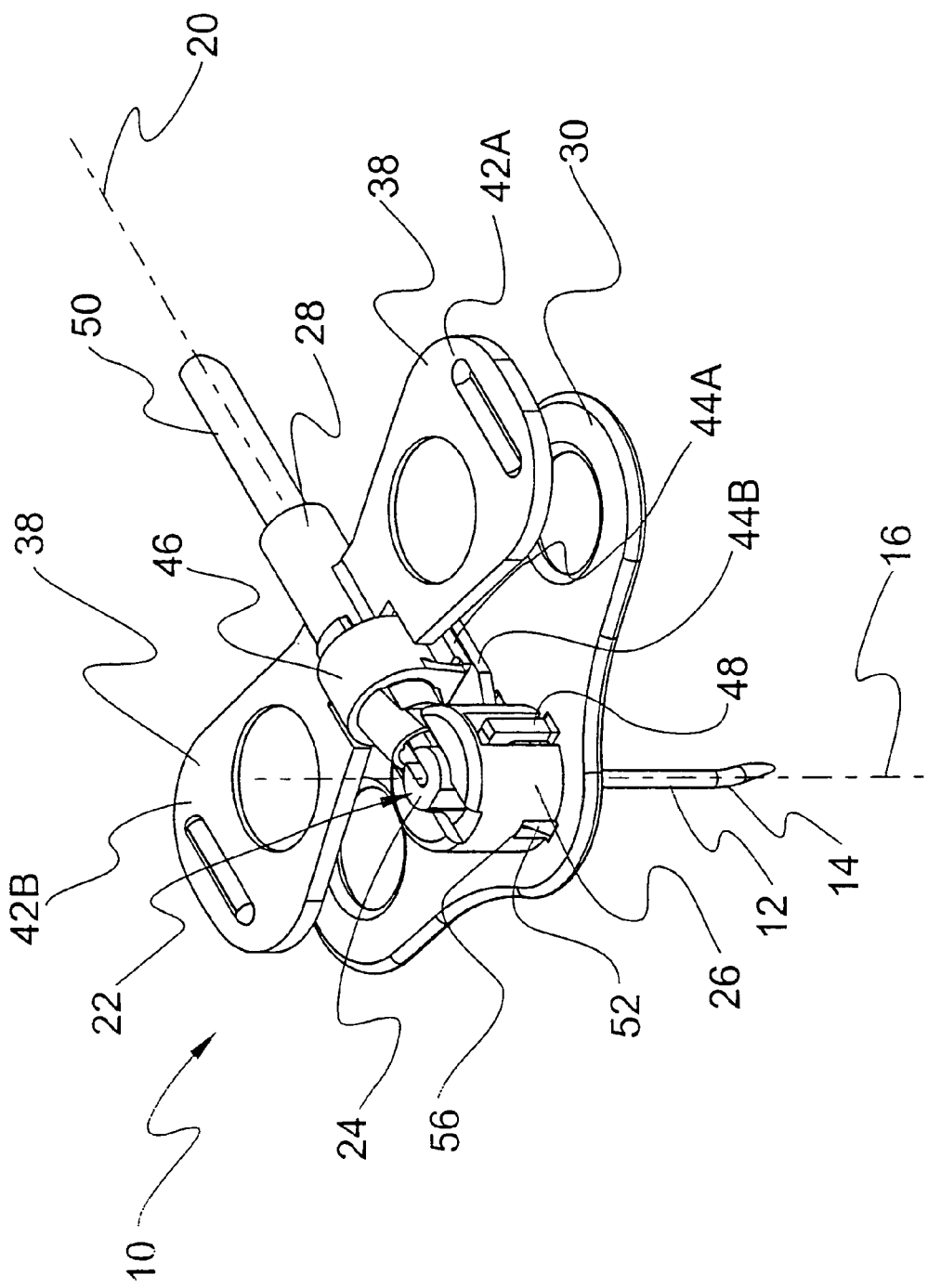
FIG. 1 is a perspective view of a needle safety apparatus adapted for use with a Huber needle in a fully unshielded configuration according to an illustrative embodiment of the present disclosure.
Figure 2:
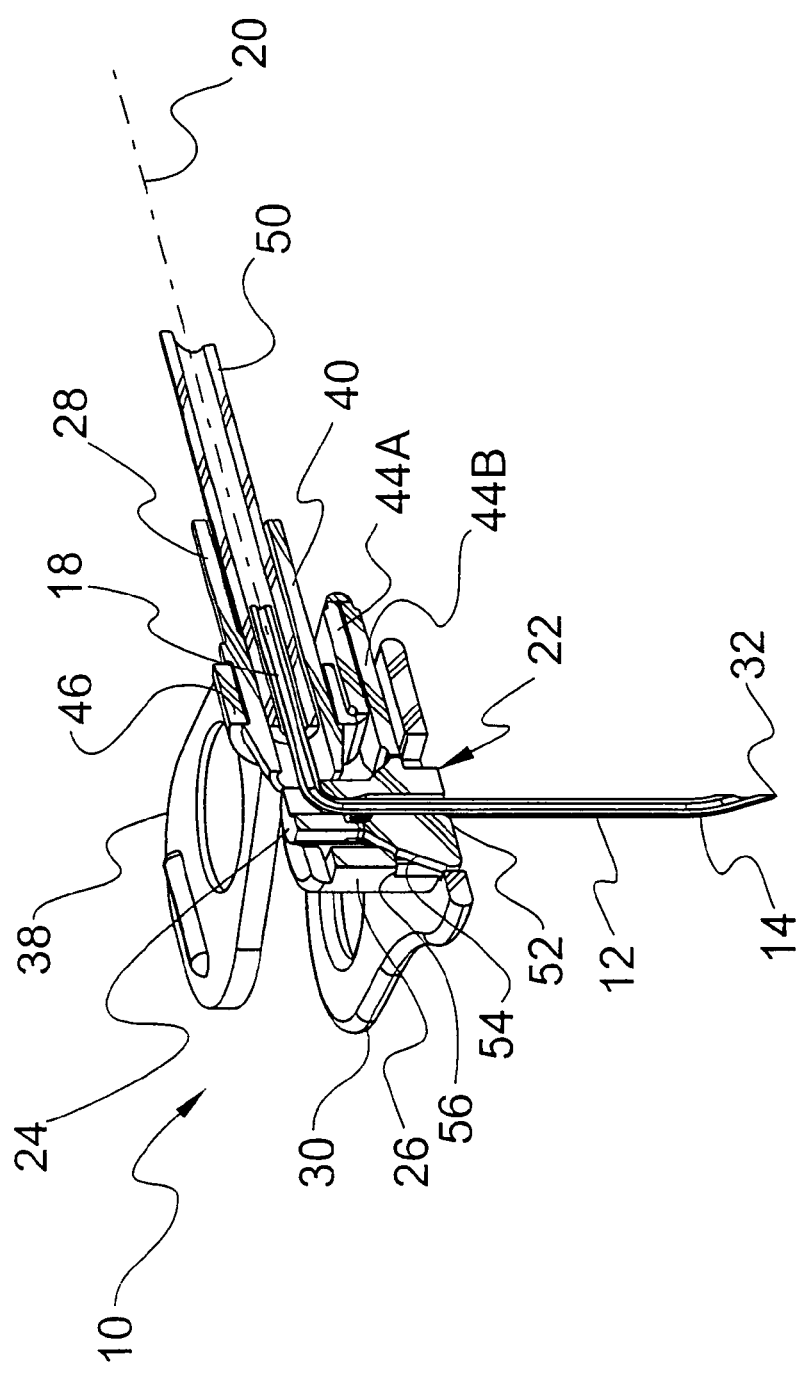
FIG. 2 is a cross sectional perspective view of a needle safety apparatus adapted for use with a Huber needle in a fully unshielded configuration according to an illustrative embodiment of the present disclosure.
Figure 3:
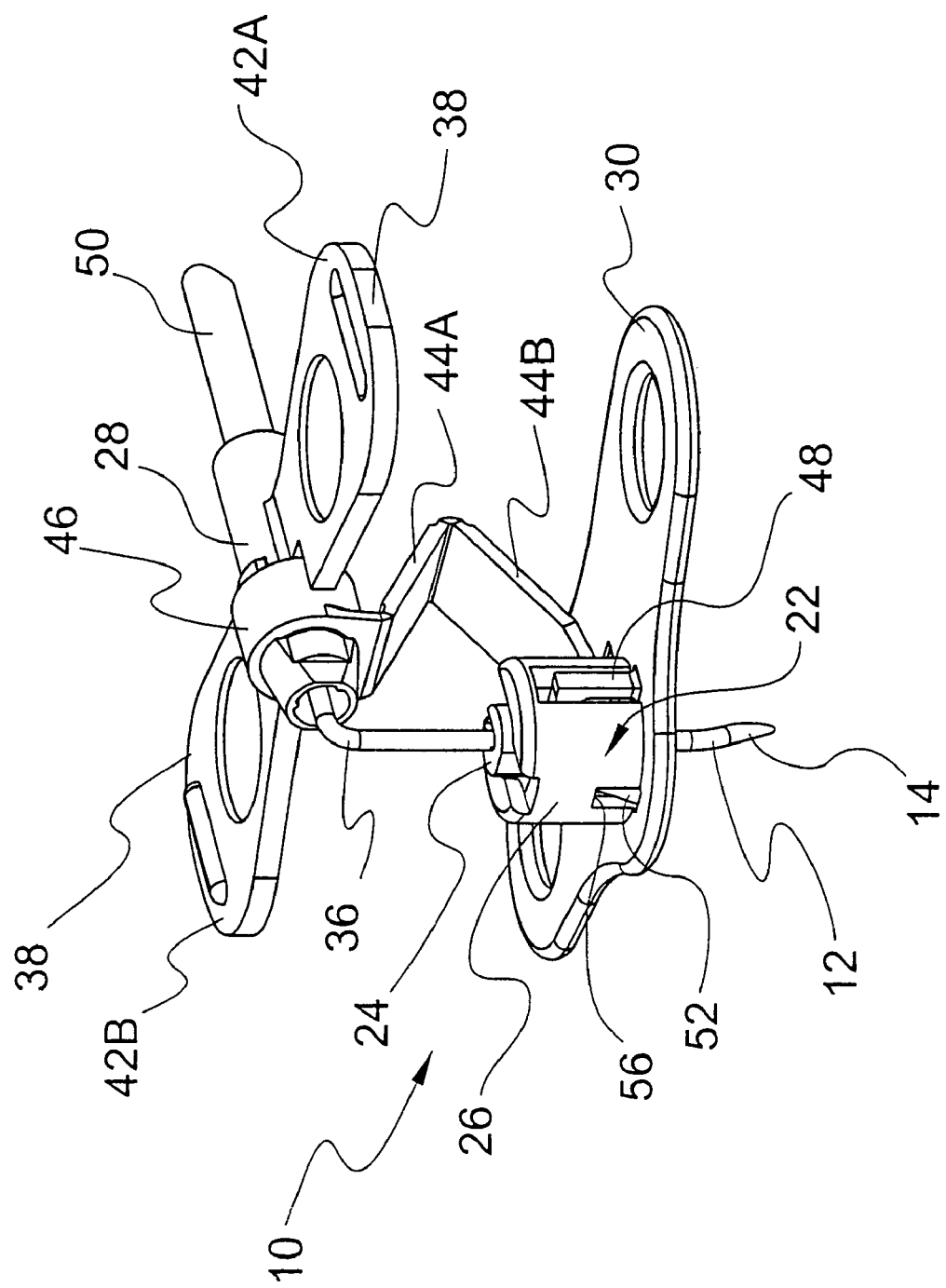
FIG. 3 is a perspective view of a needle safety apparatus adapted for use with a Huber needle in a partially retracted configuration according to an illustrative embodiment of the present disclosure.
Figure 4:
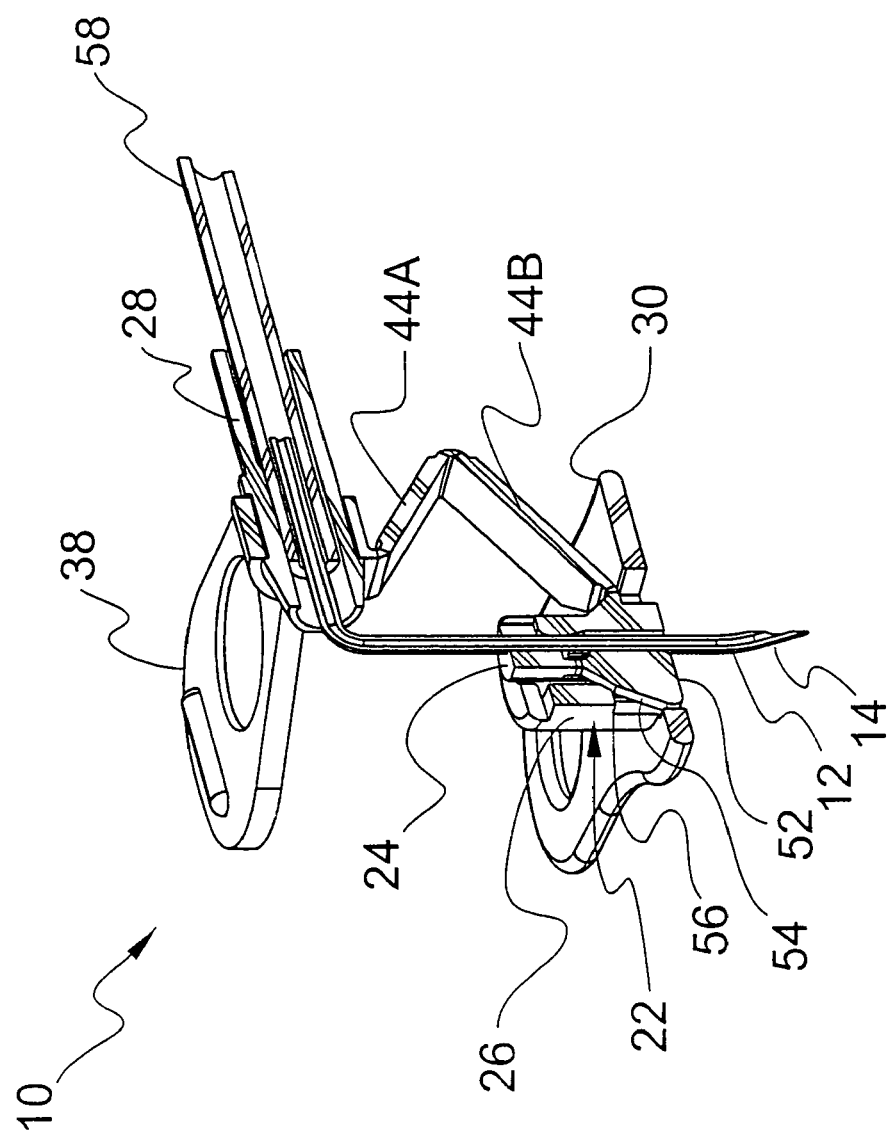
FIG. 4 is a cross sectional perspective view of a needle safety apparatus adapted for use with a Huber needle in a partially retracted configuration according an illustrative embodiment of the present disclosure.
Figure 5:
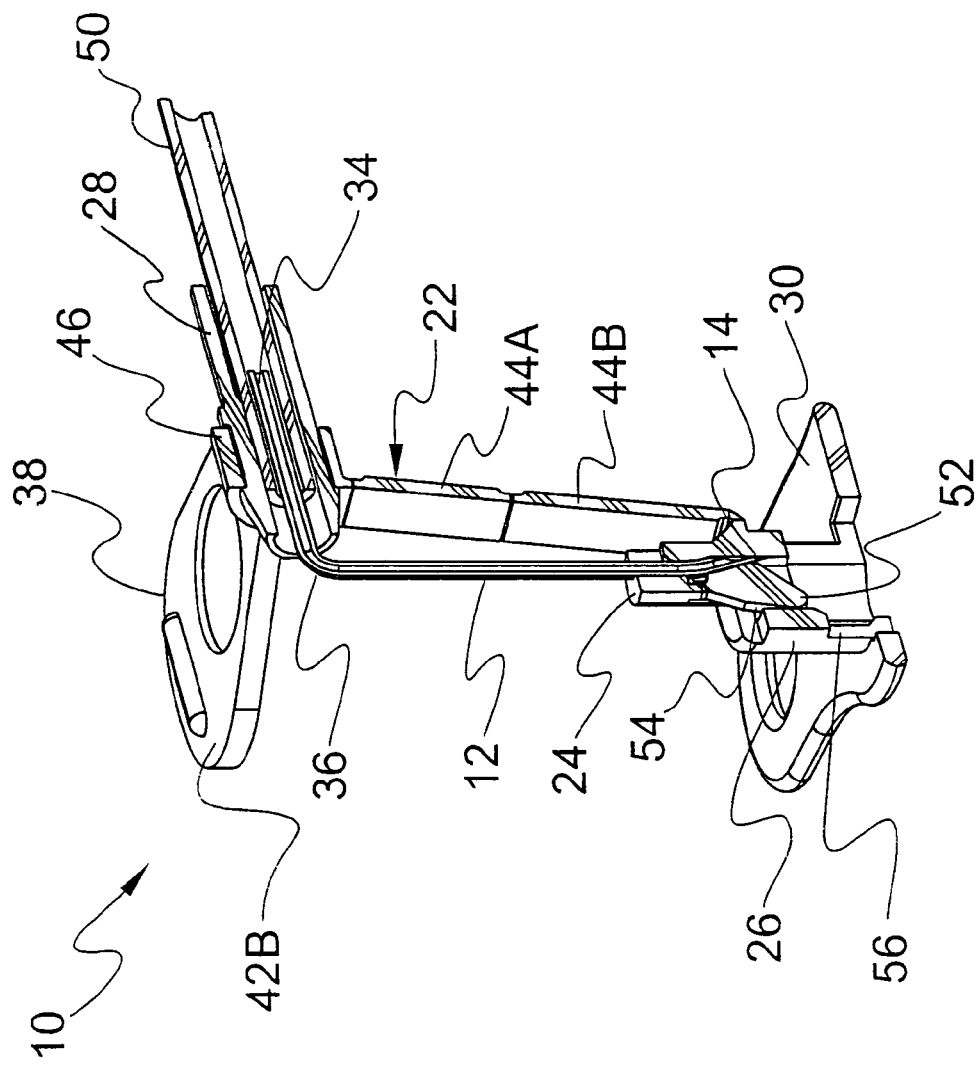
FIG. 5 is a cross sectional perspective view of a needle safety apparatus adapted for use with a Huber needle in a retracted unlatched configuration according to an illustrative embodiment of the present disclosure.
Figure 6:
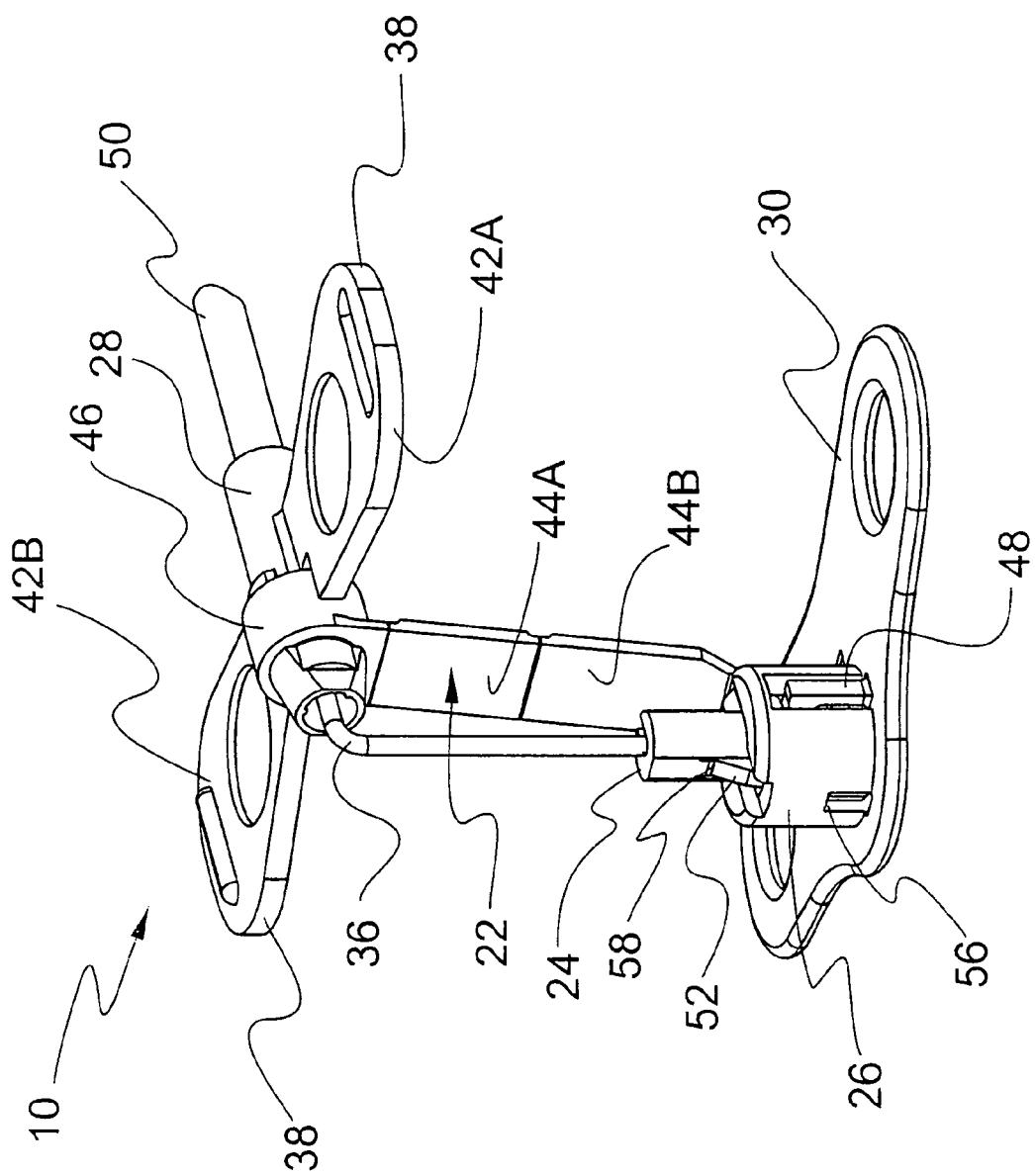
FIG. 6 is a perspective view of a needle safety apparatus adapted for use with a Huber needle in a shielded and latched configuration according to an illustrative embodiment of the present disclosure.
Figure 7:
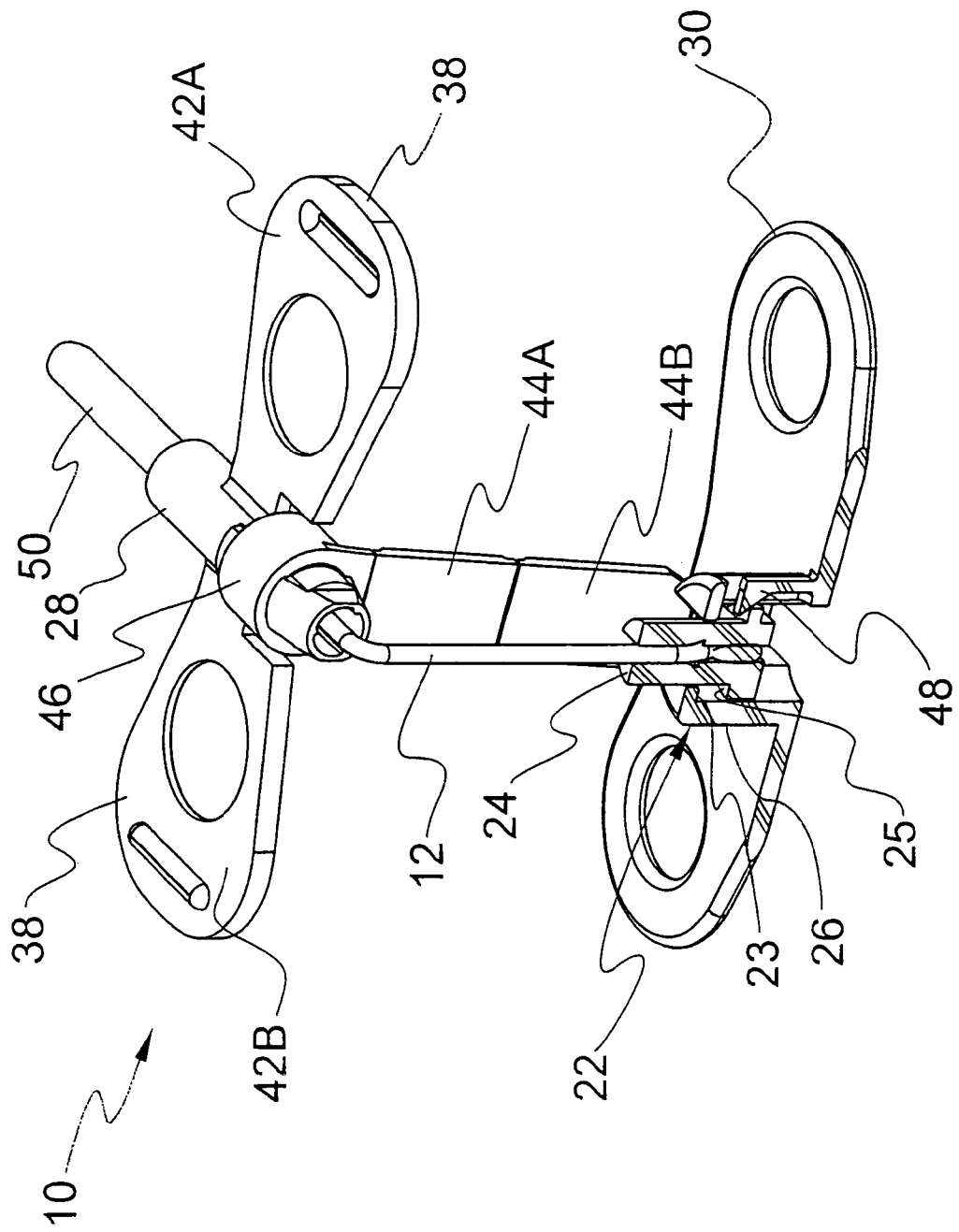
FIG. 7 is a cross sectional perspective view of a needle safety apparatus adapted for use with a Huber needle in a shielded and latched configuration according to an illustrative embodiment of the present disclosure.
Figure 8:
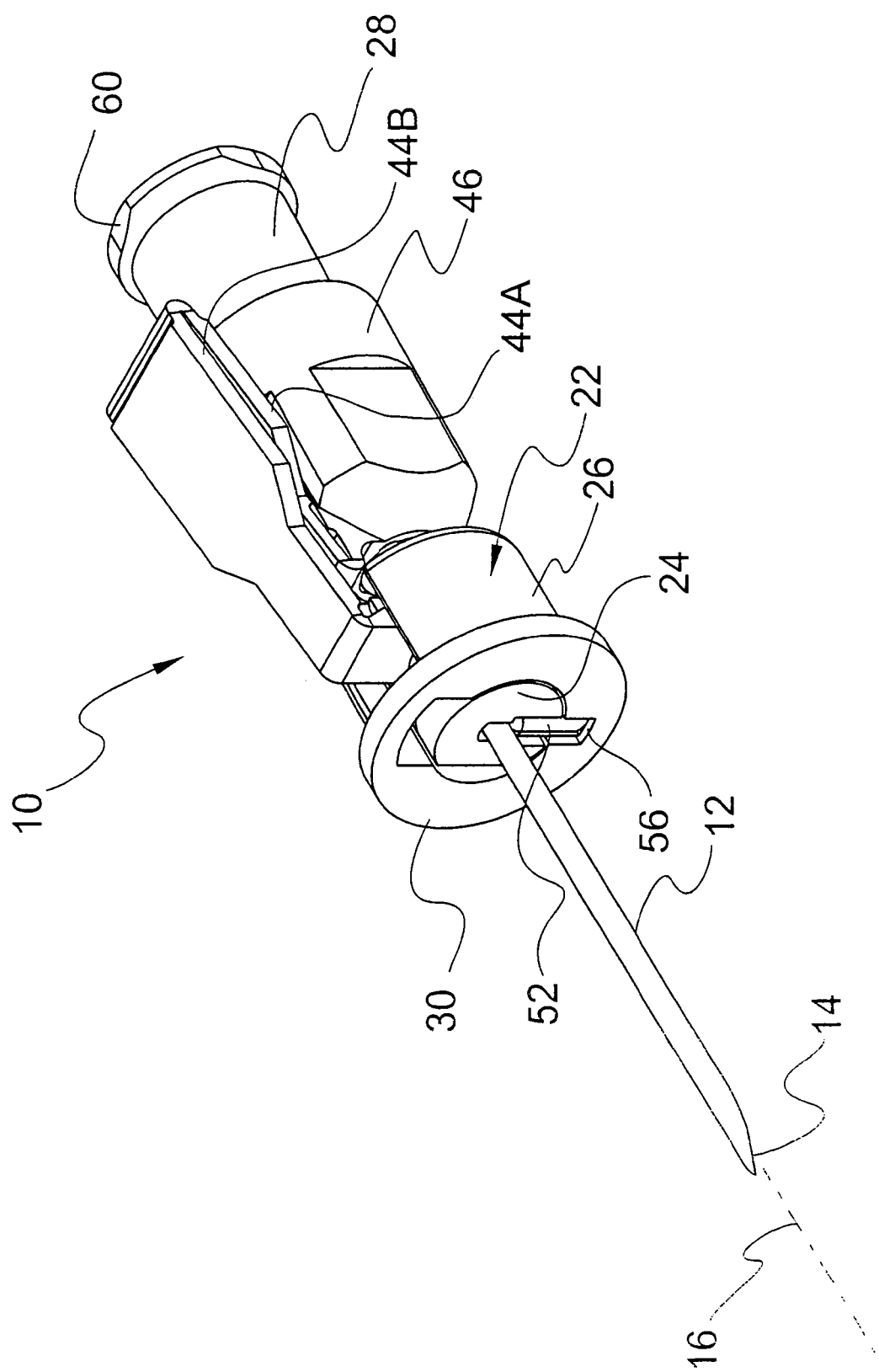
FIG. 8 is a perspective view of a needle safety apparatus adapted for use with a syringe needle in a fully unshielded configuration according to an illustrative embodiment of the present disclosure.
Figure 9:
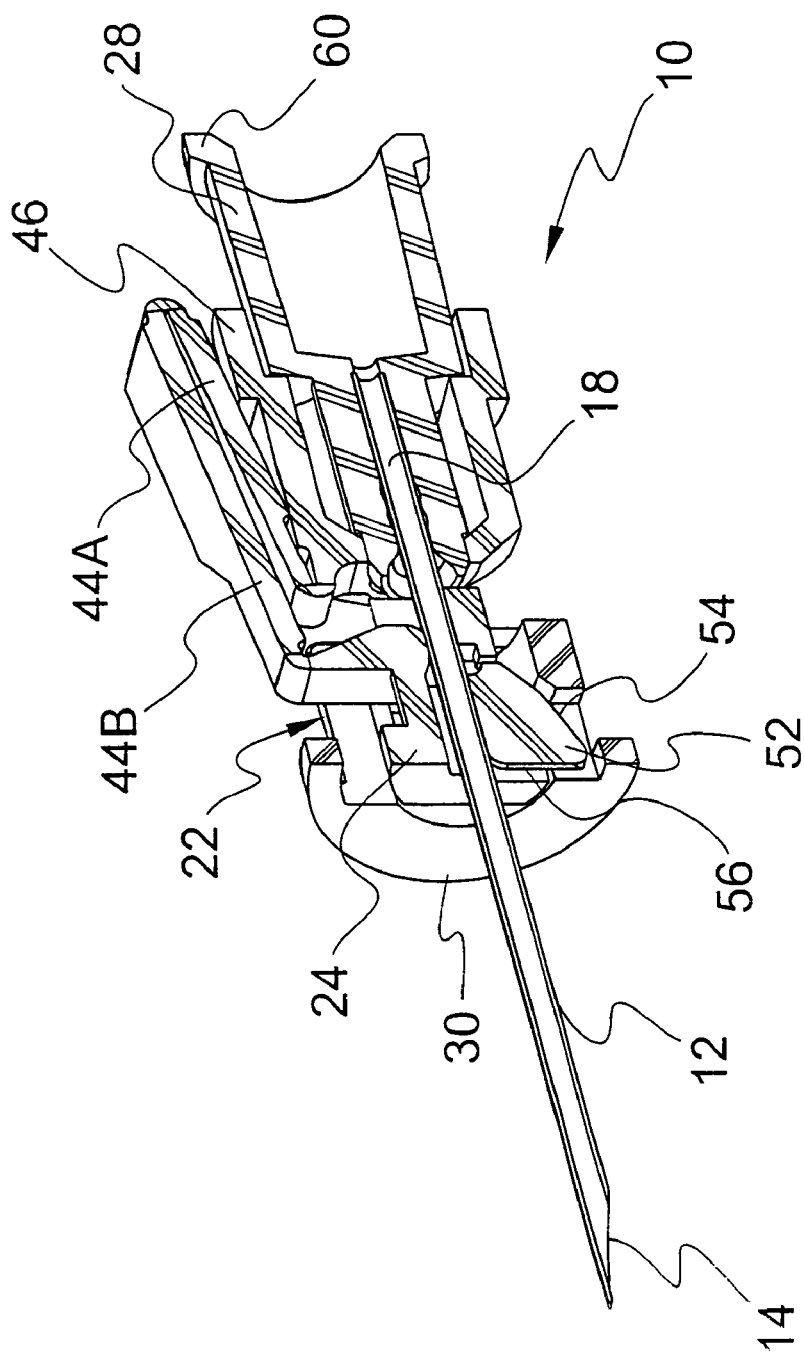
FIG. 9 is a cross sectional perspective view of a needle safety apparatus adapted for use with a syringe needle in a fully unshielded configuration according to an illustrative embodiment of the present disclosure.
Figure 10:
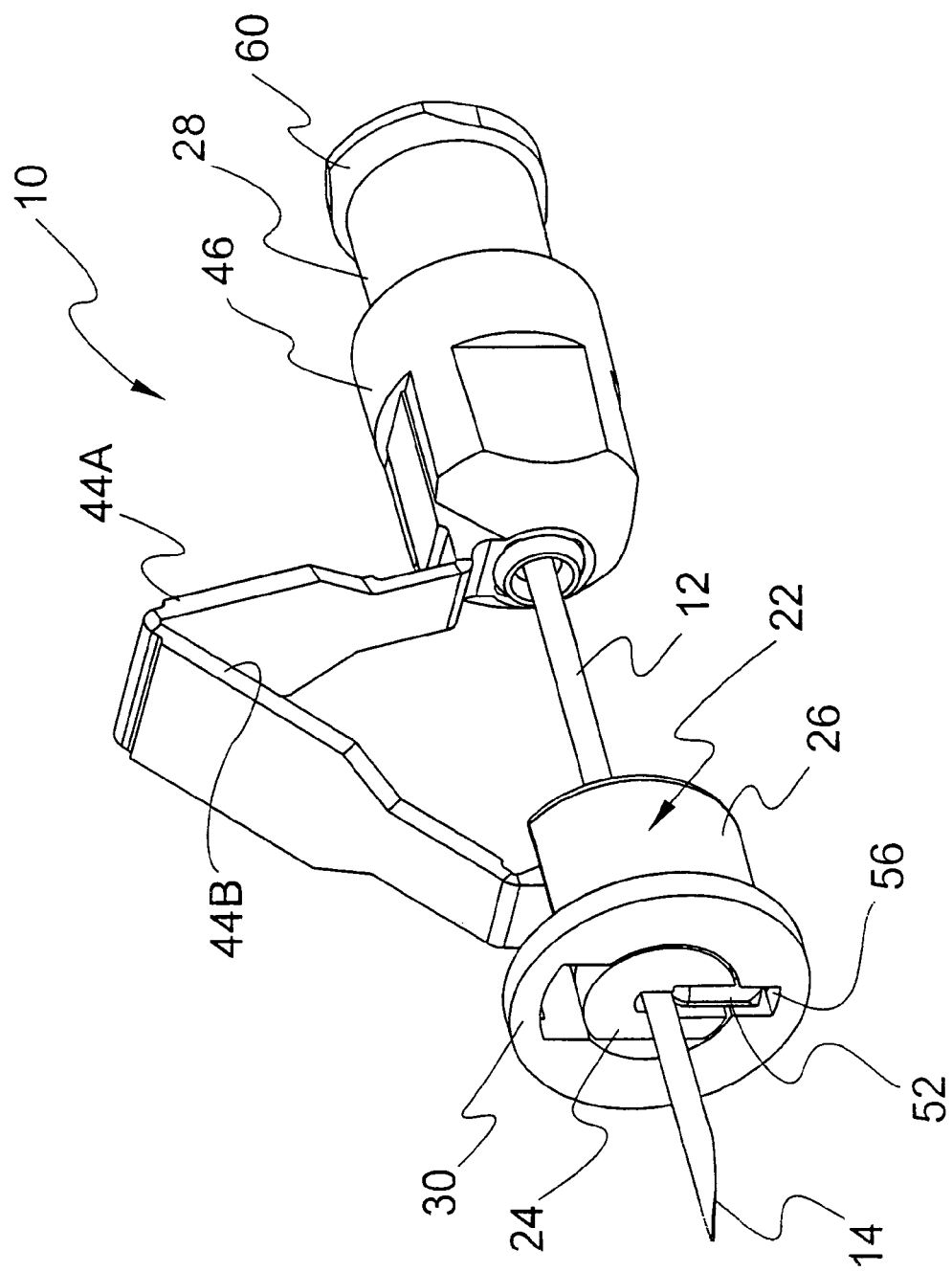
FIG. 10 is a perspective view of a needle safety apparatus adapted for use with a syringe needle in a partially retracted configuration according to an illustrative embodiment of the present disclosure.
Figure 11:
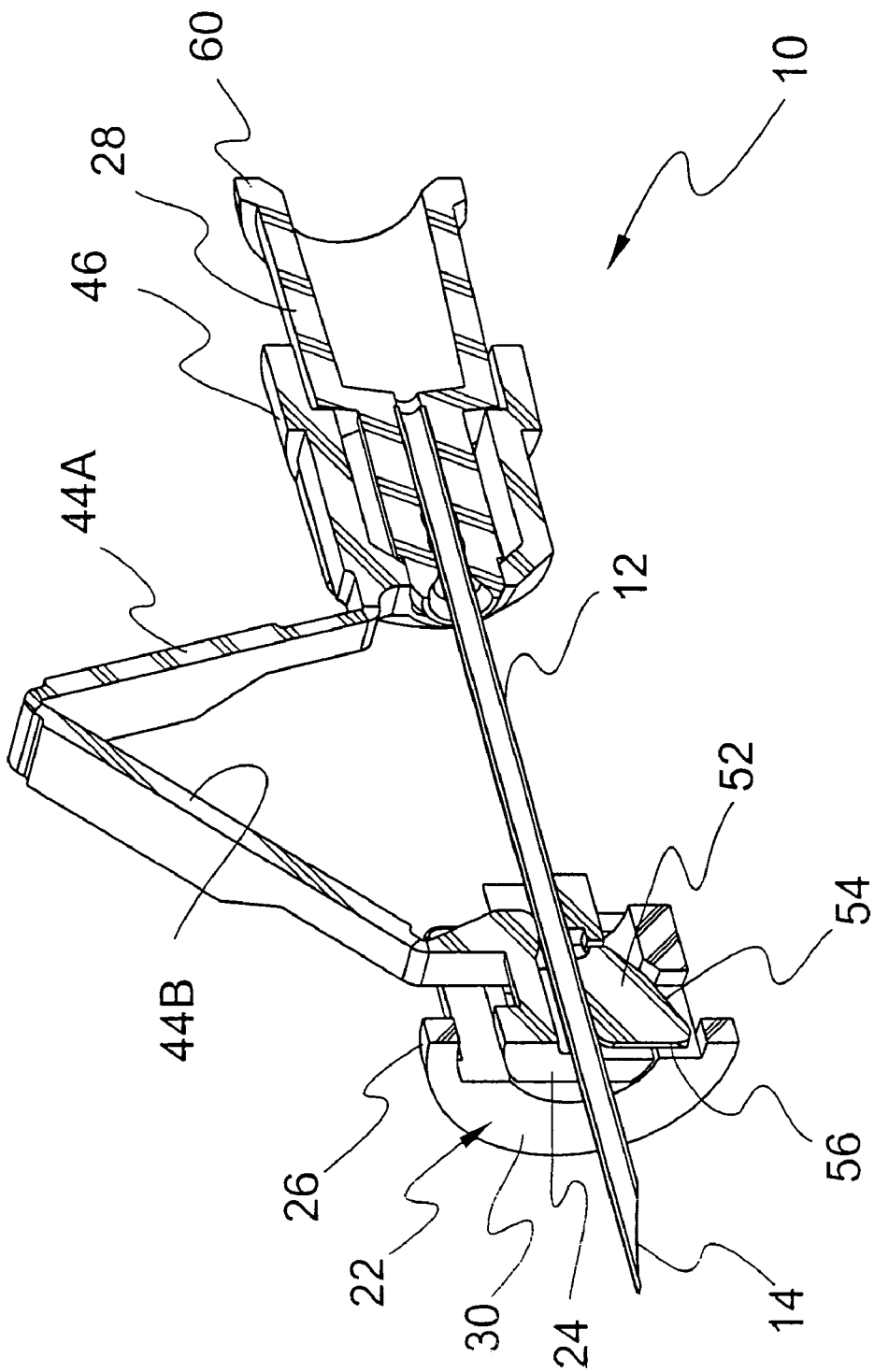
FIG. 11 is a cross sectional perspective view of a needle safety apparatus adapted for use with a syringe needle in a partially retracted configuration according to an illustrative embodiment of the present disclosure.
Figure 12:
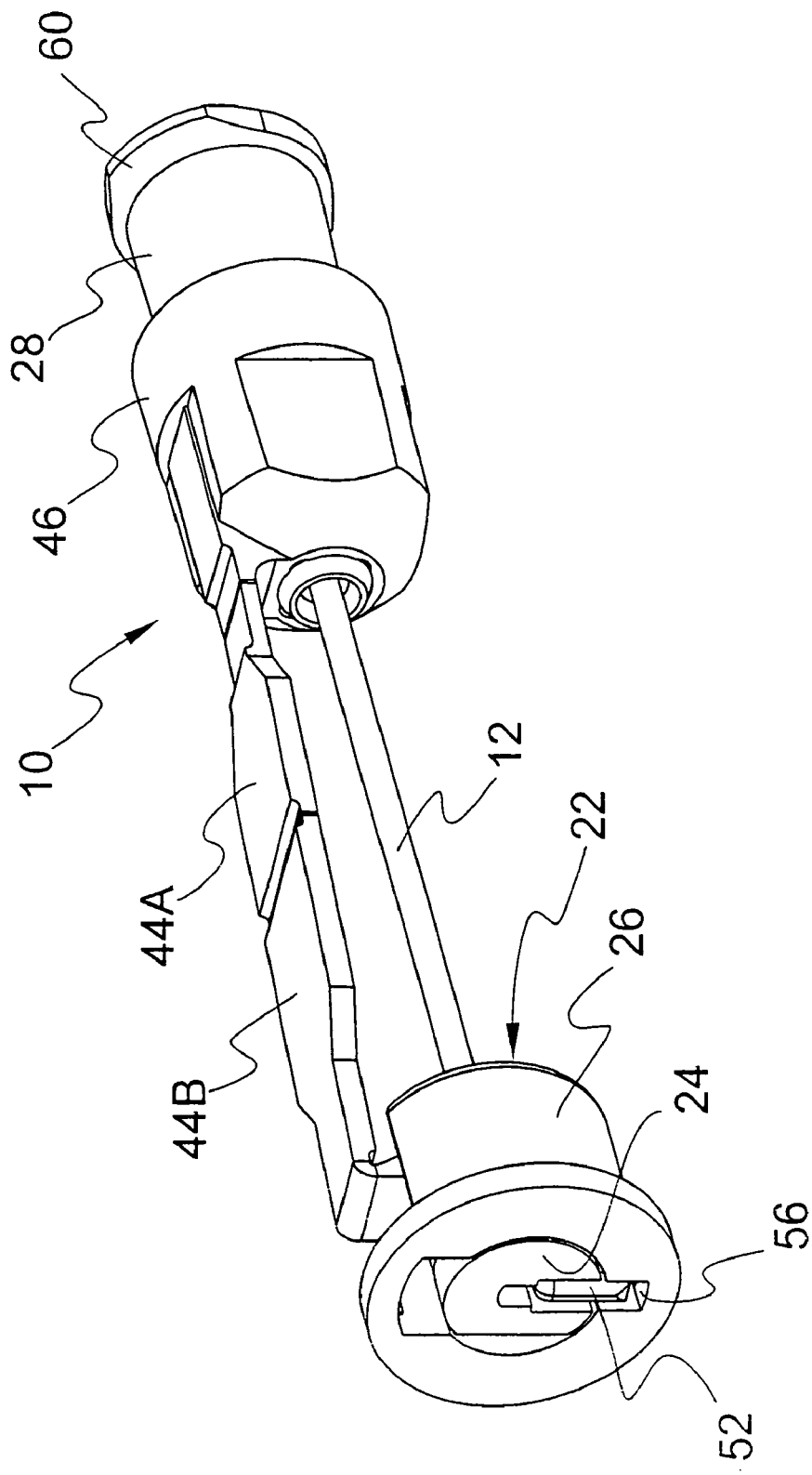
FIG. 12 is a perspective view of a needle safety apparatus adapted for use with a syringe needle in a retracted unlatched configuration according to an illustrative embodiment of the present disclosure.
Figure 13:
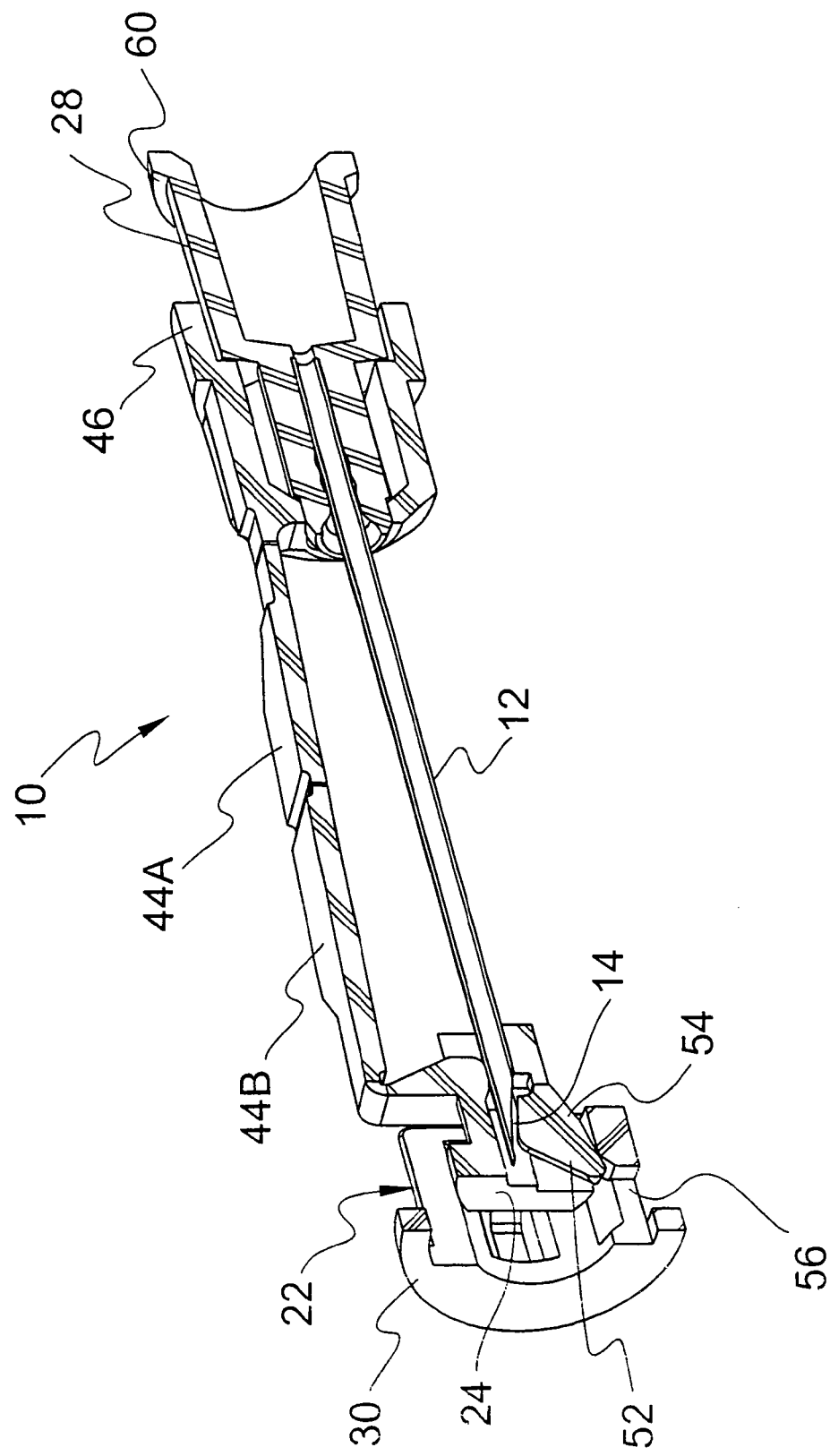
FIG. 13 is a cross sectional perspective view of a needle safety apparatus adapted for use with a syringe needle in a retracted unlatched configuration according to an illustrative embodiment of the present disclosure.
Figure 14:
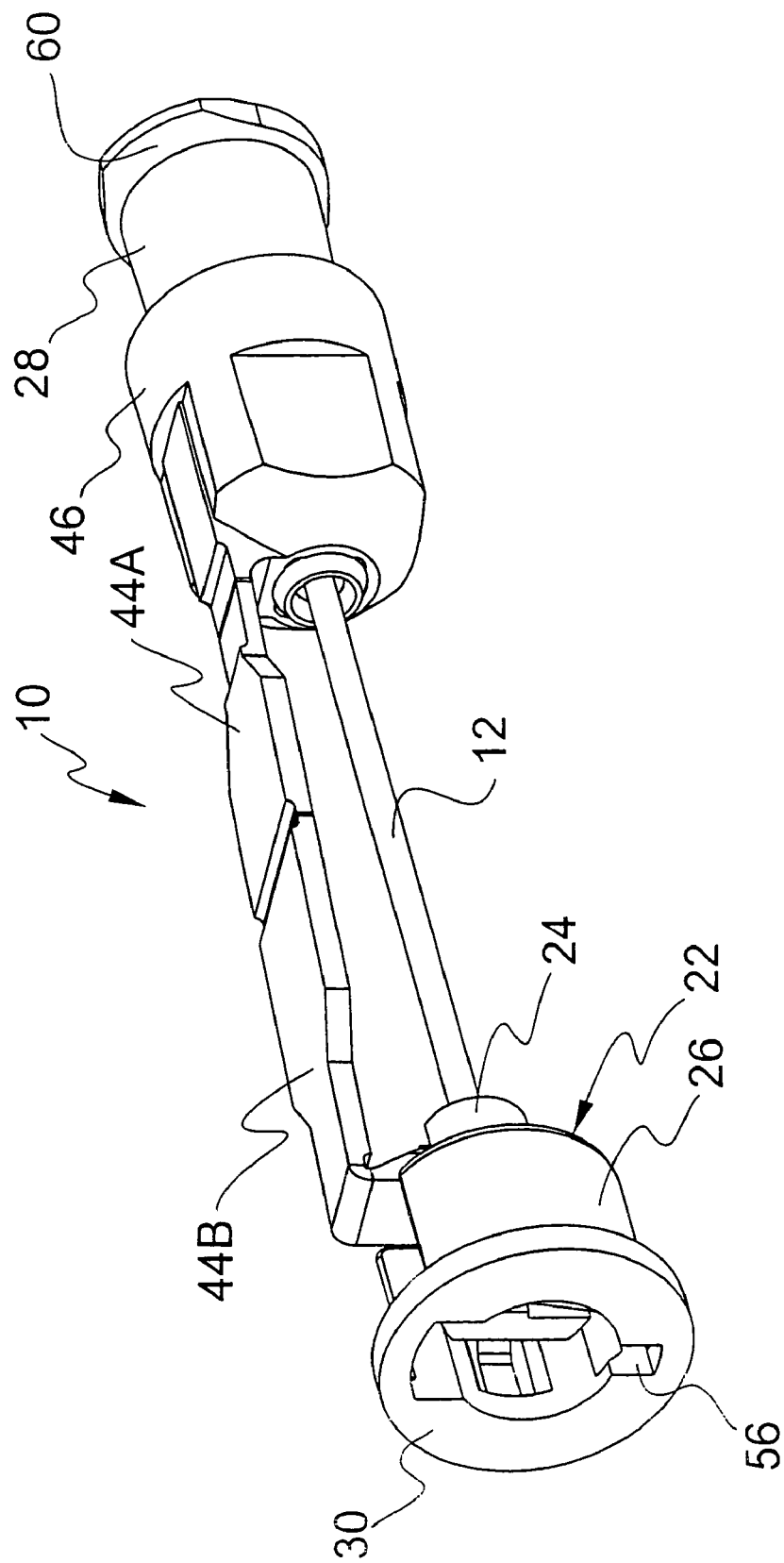
FIG. 14 is a perspective view of a needle safety apparatus adapted for use with a syringe needle in a shielded and latched configuration according to an illustrative embodiment of the present disclosure.
Figure 15:
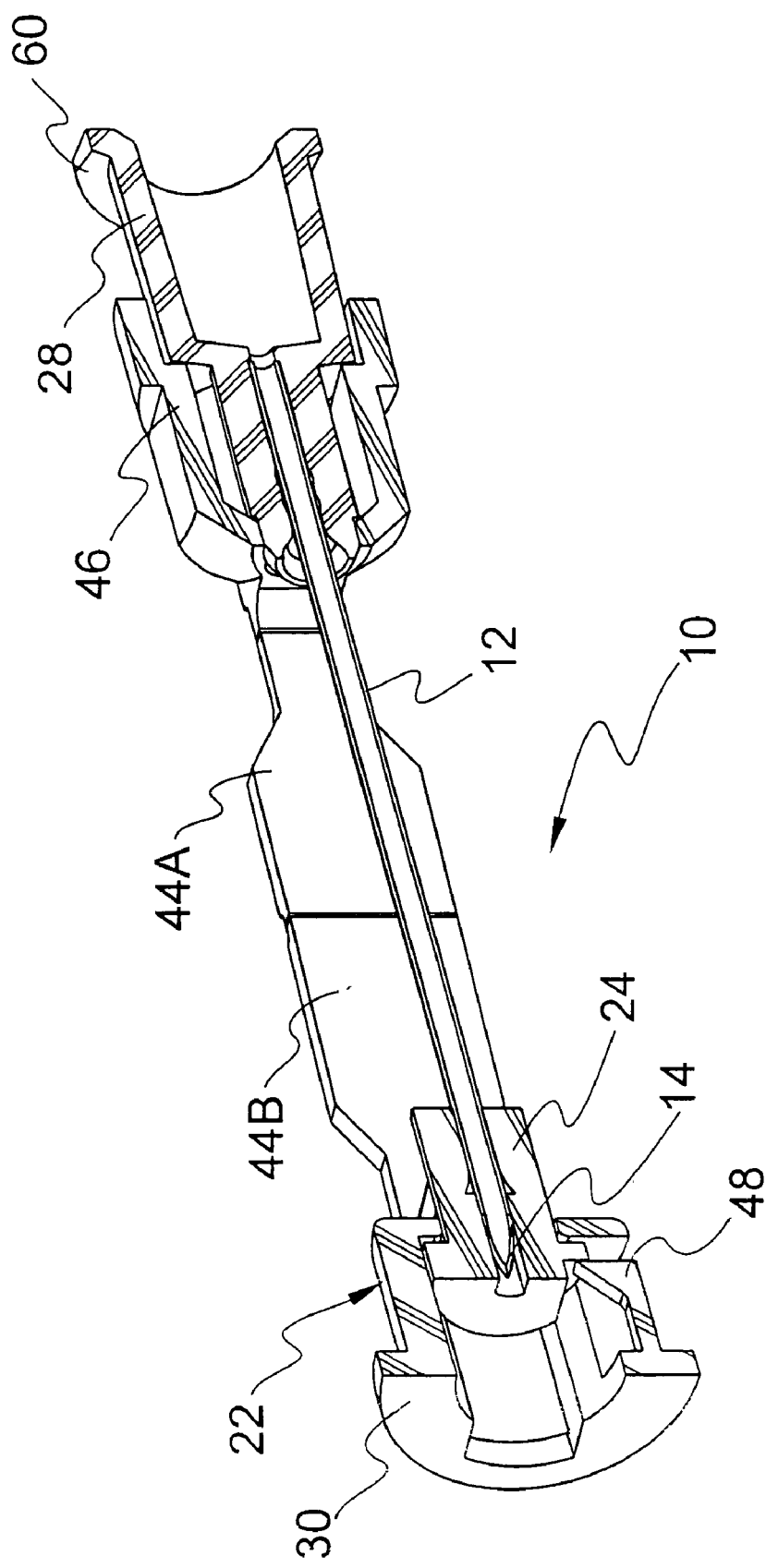
FIG. 15 is a cross sectional perspective view of a needle safety apparatus adapted for use with a syringe needle in a shielded and latched configuration according to an illustrative embodiment of the present disclosure.

Turning now to the figures wherein like components are designated by like reference numerals throughout the several views. Referring initially to FIGS. 1-7, there is illustrated one embodiment of a needle safety apparatus 10, constructed in accordance with the principals of the present disclosure. The embodiment includes a needle 12 having a distal portion 14 defining a longitudinal axis 16 which is angularly displaced relative to a transverse axis 20 defined by a proximal portion 18 of needle 12. A shield assembly 22 is mounted with needle 12 and extensible, via an inner bearing 24 and outer bearing 26, between a retracted position (FIGS. 1-2) and an extended position (FIG. 6) via intermediate positions (FIGS. 3-5). This embodiment of a needle safety apparatus 10 is advantageously configured to prevent hazardous exposure to a needle 12 by providing an adequate and reliable safety shield apparatus for port access needle devices as will be discussed below.

The embodiment of needle safety apparatus 10 as discussed below includes a hub 28 mounted with the proximal portion 18 of needle 12 and a planar contact surface 30 mounted with outer bearing 26. It is envisioned that planar contact surface 30 may be hingedly or fixedly attached to outer bearing 26. The needle safety apparatus 10 according to the present embodiment includes a shield assembly 22 which is extensible between a retracted position and an extended position via fixed positioning of planar contact surface 30 relative to movement of needle 12 along longitudinal axis 16. Thus, another advantage of the present disclosure is that needle safety apparatus 10 is actuated without applying substantial transverse forces to needle 12 during removal, thus providing a higher degree of safety to the clinician and subject. Further, this configuration of needle safety apparatus 10 advantageously provides an automatic shielding of needle 12 as shield assembly 22 is manipulated to the extended position as will be discussed.

Needle safety apparatus 10 is contemplated for use in the field of medical fluid infusion and/or collection. At least one embodiment of needle safety apparatus 10 is envisioned to be a disposable port access needle device employing, among other things, safety features having shielding capabilities to prevent inadvertent sticking or punctures of clinicians and subjects, as well as uniform and dependable movement of shield assembly 22 during a procedure and a locking mechanism for reliable use. The above advantages, among others, realized from the present disclosure are attained through the disclosed needle safety apparatus 10, which is extensible to a protective configuration, as discussed hereinbelow. These features of the present disclosure advantageously facilitate a safe infusion and/or collection of fluids and prevent inadvertent needle stick of a clinician and subject.

The component parts of needle safety apparatus 10 may be fabricated from a material suitable for medical applications, such as, for example, polymerics or metals, such as stainless steel, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate. Needle safety apparatus 10 may be integrally assembled of its constituent parts. Alternatively, portions of safety shield apparatus 10 can be monolithically formed and assembled therewith.

Referring to FIGS. 1-7, needle safety apparatus 10 is employed with an angled needle 12, such as a Huber type safety needle and includes a needle 12, a needle hub 28, a shield assembly 22 and a section of medical tubing 50.

In the illustrative embodiment, the needle 12 is formed from an angled cannula. Generally, for the purposes of providing access to medical needle 12 along a plane orthogonal to a line of percutaneous entry and parallel to a plane of an entry site, medical needle 12 is angled. This configuration is consistent with a Huber type safety needle. Other angled medical needles may be protected by the apparatus in accordance with the present disclosure. The distal portion 14 of medical needle 12 has an inferiorly disposed sharpened end 32. The proximal portion 18 includes a superiorly disposed abrupt end 34 and a medially disposed bend 36 is formed therebetween.

Needle hub 28 includes a winged portion 38 by which needle hub 28 is grasped and displaced. Needle hub 28 includes an open proximal end configured to accept a tubing segment, and a proximal end configured to accept and securely retain the proximal end of needle which is disposed in the end of said tubing in the interior cavity of the needle hub 28 Winged portion 38 includes a digital (manipulable) interface which may be facilely gripped by a clinicians fingers. Winged portion 38 may include two winged parts 42A, 42B. Winged parts 42A, 42B may be hinged or flexible and horizontally disposed, as shown in FIGS. 1-5 to provide a low silhouette until needle safety apparatus 10 is to be removed from an insertion site. This configuration advantageously permits less obstruction for tape down and other site preparation over extended periods of use.

Winged parts 42A, 42B may be articulated to a more vertical orientation (not shown) when extracting medical needle 12. Winged portion 38 permits extraction forces to be applied directly above and in-line with a longitudinal axis insertion line of medical needle 12. To aid in gripping and transferring extraction forces to winged portion 38, winged parts 42A, 42B may include corrugation, texturing or other process to increase surface friction.

The manufacture of needle safety apparatus 10 parts may be accomplished by injection molding of needle hub 38 and shield assembly 22, both of which may be injection molded using synthetic resinous material, such as polypropylene. Medical tubing 50 may be selected from medical tubing currently commercially available. To assemble needle safety apparatus 10, distal portion 14 of needle 12 can be assembled to shield assembly 22, and the shield assembly snapped over the outside surface of needle hub 28. Tubing 50 may be displaced through the proximal opening of needle hub 28 as previously disclosed. The proximal end of medical needle 12 is displaced into tubing 50 and securely affixed thereat.

Needle safety apparatus 10 may be properly sterilized and otherwise prepared for storage, shipment and use. Needle safety apparatus 10 may be properly affixed, via planar contact surface 30, and inserted within a subject (not shown) for a port access medical procedure, such as, for example, one or a plurality of infusion and/or collection of fluid procedures. Upon completion of the medical procedure(s), force may be applied to the proximal surface of planar contact surface 30 while retracting forces are applied to winged parts 42A, 42B. Thus, planar contact surface 30 remains in a fixed position, relative to movement of shield assembly 22 to the extended position.

Inner bearing 24 and outer bearing 26 slidably support medical needle 12 to facilitate extension of shield assembly 22 during extraction. Medical needle 12 is thereby extracted from an insertion site. As medical needle 12 is extracted, needle hub 28 is displaced away from planar contact surface 30 unfolding hinged portions 44A, 44B. Proximal hinged portion 44A is hingedly attached to collar 46 and to hinged portion 44B. Collar 46 may be monolithically formed with hub 28. Hence, any reference to hinge portion 44A connected to hub 28 includes connection to collar 46 or connection directly to hub 28. Hinged portion 44B is hingedly attached to inner bearing 24. The purpose and function of hinged portions 44A, 44B is to serve as a tether for preventing extension of the shield assembly 22 beyond the distal portion 14 of needle 12. It is envisioned that the tether may be in the form of a cord, strap or the like (not shown). Collar 46 is rigidly retained, for example by snap features, to hub 28. Shield assembly 22 is thereby articulated until the sharpened tip of medical needle 12 is displaced into protective shielding of shield assembly 22. Inner bearing 24 and outer bearing 26 are unreleasably, respectively engaged by latching arm 48. As shown in FIGS. 4 and 5, the sharpened tip of medical needle 12 is fully enclosed by shield assembly 22.

In the illustrative embodiment, outer bearing 26 is monolithically formed with planar contact surface 30 as a substantially cylindrical structure protruding from the proximal surface of planar contact surface 30. Inner bearing 24 is a smaller substantially cylindrical structure disposed within the walls of the outer cylinder 26. Outer bearing 26 thus forms a guide for linear translation of the inner cylinder 24 along longitudinal axis 16, while inner bearing 24 forms a guide for linear translation of needle 12.

A latching arm 48 is formed in the sidewall of outer bearing 26. The latching arm 48 allows inner cylinder 24 to translate telescopically when pulled by extended (unfolded) hinged portions 44A, 44B as hub 28 is displaced away from planar contact surface 30. When shield assembly 22 is fully extended, the sharpened tip of needle 12 is retracted safely within shield assembly 22. The latching arm 48 prevents inner bearing 48 from retracting telescopically in a distal direction thus retaining the shield assembly 22 in a fully extended configuration. It is also contemplated that latching arm 48 may be formed in the sidewall of inner bearing 24. A flange 23 on outer bearing 26 interacts with flange 25 on inner bearing 24 as shield assembly 22 is distally extended to retain outer bearing 26 with the shield assembly 22 in a fully extended configuration.

In an illustrative embodiment, a wedging portion 52 secures the distal portion 14 of needle 12 within inner bearing 24. Wedging portion 52 is pivotally mounted to inner bearing 24 (FIGS. 2, 4 and 5) or pivotally formed with the inner bearing, for example, by forming a living hinge 58. When needle 12 is extended and unshielded, wedging portion 52 is disposed through a cutout 56 in the sidewall of outer bearing 26. Pivoting of wedging portion 52 occurs when inner bearing 24 is extended telescopically in the proximal direction relative to outer bearing 26. Cam surface 54 of wedging portion 52 engages the proximal edge of cutout 56 thus pivotally displacing wedging portion 52 within the inner space of inner bearing 24. It is also contemplated that cutout 56 may also comprise an enclosed space. Further, wedging portion 52 may embody various shapes to accomplish the function of securing the distal portion 14 of needle 12 within inner bearing 24.

Referring now to FIGS. 8-15, an embodiment of the needle safety apparatus is disclosed for use, for example, with a straight needle 12 and luer fitting 60 for use with a medical syringe. In this embodiment needle hub 28 is be configured to include a luer fitting 60 for attachment to various needle devices such as a syringe or IV set (not shown).

Needle hub 28 is firmly and securely affixed to the needle 12. Collar 46 is adapted for press fit or snapping engagement over needle hub 28. Planar contact surface 30 is formed as a flange at the distal edge of outer bearing 26. Operation of the needle safety device with a straight needle is substantially identical to operation with an angled needle apparatus as described hereinbefore.

Inner bearing 24 and outer bearing 26 slidably support medical needle 12 to facilitate extension of shield assembly 22 during extraction. Medical needle 12 is thereby extracted from an insertion site. As medical needle 12 is extracted, needle hub 28 is displaced away from planar contact surface 30 unfolding hinged portions 44A, 44B. Proximal hinged portion 44A is hingedly attached to collar 46 and to hinged portion 44B. Hinged portion 44B is hingedly attached to inner bearing 24. Collar 46 is rigidly retained, for example, by snap features to hub 28. Shield assembly 22 is thereby articulated until the sharpened tip of medical needle 12 is displaced into protective shielding of shield assembly 22. Inner bearing 24 and outer bearing 26 are unreleasably engaged by latching arm 48, respectively. As shown in FIGS. 12-15, the sharpened tip of medical needle 12 is fully enclosed by shield assembly 22.

A latching arm 48 (FIG. 15) is formed in the sidewall of outer bearing 26. The latching arm 48 allows inner cylinder 24 to translate telescopically when pulled by extended (unfolded) hinged portions 44A, 44B as hub 28 is displaced away from planar contact surface 30. When shield assembly 22 is fully extended, the distal portion 14 of needle 12 is retracted safely within shield assembly 22. The latching arm 48 prevents inner bearing 24 from retracting telescopically in a distal direction thus retaining the shield assembly 22 in a fully extended configuration.

In an illustrative embodiment, a wedging portion 52 secures the distal end 14 of needle 12 within inner bearing 24. Wedging portion 52 is pivotally mounted to inner bearing 24 or pivotally formed with the inner bearing, for example, by forming a living hinge 58. When needle 12 is extended and unshielded, wedging portion 52 is disposed through a cutout 56 in the sidewall of outer bearing 26. It is also contemplated that the cutout 56 may be an enclosed area providing clearance for wedging portion 52. The pivoting of wedging portion 52 occurs when inner bearing 24 is extended telescopically in the proximal direction relative to outer bearing 26. Cam surface 54 of wedging portion 52 engages the proximal edge of cutout 56 thus pivotally displacing wedging portion 52 to secure the distal portion 14 of needle 12 within the inner space of inner bearing 24.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A medical needle shield apparatus comprising:
   a shield being extensible from a retracted position to an extended position to enclose a distal end of a needle, said needle including a proximal end mounted to a hub and said shield comprising:
   an outer bearing having a sidewall defining a first interior space about a longitudinal axis;
   an inner bearing having a sidewall defining a second interior space about said longitudinal axis, wherein said needle is disposed in said second interior space and is movable along said longitudinal axis;
   said inner bearing disposed in said first interior space and moveable therein along said longitudinal axis;
   a wedging portion movable with said inner bearing for wedging against said needle to secure the distal end of said needle within the second interior space in the extended position, wherein said wedging portion includes a cam surface which engages a sidewall of said outer bearing to pivot said wedging portion when said inner portion is moved along said longitudinal axis; and a tether having a proximal end connected to said hub and a distal end connected to said inner bearing for preventing separation of the shield from the needle in the extended position.

2. The needle safety apparatus according to claim 1, wherein said wedging portion is pivotably mounted to said interior bearing and includes a cam surface which engages said outer bearing sidewall to pivot said wedging portion to an occluding position when said inner bearing is moved along said longitudinal axis.

3. The needle safety apparatus according to claim 2, wherein said outer bearing sidewall includes a cutout extending at least partially therethrough, said cutout providing clearance for said wedging portion when said wedging portion is pivoted away from said second interior space.

4. The needle safety apparatus according to claim 3, wherein said cutout includes a distal surface which engages said cam surface to pivot said wedging portion.

5. The needle safety apparatus according to claim 3, wherein said outer bearing sidewall includes an enclosed space extending from the sidewall, said enclosed space providing clearance for said wedging portion when said wedging portion is pivoted away from said second interior space.

6. The needle safety apparatus according to claim 1, wherein said outer bearing includes a distal end having a planar surface substantially orthogonal to said longitudinal axis.

7. The needle safety apparatus according to claim 6, wherein planar surface is hingedly attached to said outer bearing.

8. The needle safety apparatus according to claim 1, wherein said wedging portion is pivotably mounted to said inner bearing.

9. The needle safety apparatus according to claim 1, wherein said tether comprises extendable linkage segments.

10. The needle safety apparatus according to claim 1, wherein said tether comprises a cord.

11. The needle safety apparatus according to claim 1, wherein said inner bearing moves telescopically in said first interior space in response to proximal movement of said hub and extension of said extendable linkage segments.

12. The needle safety apparatus according to claim 1, wherein said outer bearing includes a latching arm extending into said first interior space to latch said inner bearing in a proximal position when said inner bearing is moved proximally along said longitudinal axis beyond said latching arm and wherein said wedging portion is thereby retained in a pivoted position.

13. The needle safety apparatus according to claim 1, wherein said inner bearing includes a latching arm extending into said second interior space to latch said outer bearing in a proximal position when said outer bearing is moved proximally along said longitudinal axis beyond said latching arm and wherein said wedging portion is thereby retained in a pivoted position.

14. The needle safety apparatus according to claim 1, wherein said needle includes a bend of about 90 degrees between said proximal and distal ends.

15. The needle safety apparatus according to claim 1, wherein said hub includes a winged portion extending therefrom, said winged portion providing a surface area for gripping.

* * * * *